United States Patent
Reine et al.

(10) Patent No.: US 12,275,694 B2
(45) Date of Patent: Apr. 15, 2025

(54) PHARMACEUTICALLY ACCEPTABLE SALTS OF [2-(3-FLUORO-5-METHANESULFONYL-PHENOXY)ETHYL](PROPYL)AMINE AND USES THEREOF

(71) Applicant: INTEGRATIVE RESEARCH LABORATORIES SWEDEN AB, Gothenburg (SE)

(72) Inventors: Inese Reine, Riga (LV); Clas Sonesson, Billdal (SE); Ross Nicholas Waters, Gothenburg (SE); Joakim Mihkel Tedroff, Danderyd (SE)

(73) Assignee: IRL 790 AB, Gothenburg (SE)

( * ) Notice: Subject to any disclaimer, the term of this patent is extended or adjusted under 35 U.S.C. 154(b) by 514 days.

(21) Appl. No.: 17/612,902

(22) PCT Filed: May 20, 2020

(86) PCT No.: PCT/EP2020/064046
§ 371 (c)(1),
(2) Date: Nov. 19, 2021

(87) PCT Pub. No.: WO2020/239568
PCT Pub. Date: Dec. 3, 2020

(65) Prior Publication Data
US 2022/0267262 A1  Aug. 25, 2022
US 2024/0343687 A2  Oct. 17, 2024

(30) Foreign Application Priority Data
May 24, 2019 (EP) .................................. 19176514
Mar. 27, 2020 (EP) .................................. 20166361

(51) Int. Cl.
C07C 317/22 (2006.01)
A61P 25/16 (2006.01)
C07C 59/255 (2006.01)

(52) U.S. Cl.
CPC ............ *C07C 317/22* (2013.01); *A61P 25/16* (2018.01); *C07C 59/255* (2013.01); *C07B 2200/13* (2013.01)

(58) Field of Classification Search
CPC .............................. C07C 317/22; A61P 25/16
See application file for complete search history.

(56) References Cited

U.S. PATENT DOCUMENTS

| | | |
|---|---|---|
| 5,767,132 A | 6/1998 | Bottcher et al. |
| 9,006,227 B2 | 4/2015 | Sonesson et al. |
| 9,120,728 B2 | 9/2015 | Sonesson et al. |

FOREIGN PATENT DOCUMENTS

| | | | |
|---|---|---|---|
| CN | 1130180 A | 9/1996 | |
| EP | 0363782 | 4/1990 | |
| JP | S51123821 A | 10/1976 | |
| JP | 2006193494 A | 7/2006 | |
| WO | WO 2002/000602 | 1/2002 | |
| WO | WO 2007/063789 | 6/2007 | |
| WO | WO 2007/072041 | 6/2007 | |
| WO | WO 2009/133107 | 11/2009 | |
| WO | WO 2009/133109 | 11/2009 | |
| WO | WO 2009/133110 | 11/2009 | |
| WO | WO-2012143337 A1 * | 10/2012 | ........... A61K 31/138 |
| WO | 2020110128 A1 | 6/2020 | |
| WO | 2020239568 A1 | 12/2020 | |

OTHER PUBLICATIONS

Jaques J, et al. (1981) Enantiomers, Racemates and Resolutions. Section 5: Formation and Separation of Diastereoisomers. pp. 251-368. John Wiley and Songs, New York.
King RE. (1985) Remington's Pharmaceutical Sciences. Part 8: Pharmaceutical Preparations and Their Manufacture, pp. 1409-1662. Maack Publishing Co., Easton PA.
Stahl PH, et al. (2002) Handbook of Pharmaceutical Salts: Properties, Selection, and Use. Wiley-VCH. pp. 1-372.
Alexander GE, et al. (1986) Parallel Organization of Functionality Segregated Circuits Linking Basal Ganglia and Cortex. Ann. Rev. Neurosci., 9: 357-381.
Bramham CR, et al. (2010) The Arc of synaptic memory. Exp. Brain Res., 200: 125-140.
Cepeda C, et al. (2010) Genetic mouse models of Huntington's disease: focus on electrophysiological mechanisms. ASN Neuro, 2(2): e00033.
Chomczynski P, et al. (1987) Single-step method of RNA isolation by acid guanidinium thiocyanate-phenol-chloroform extraction. Anal. Biochem., 162: 156-159.
Crespi CL, et al. (2000) Fluorometric screening for metabolism based drug-drug interactions.J. Pharm. Tax. Meth., 44: 325-331.
Forlin L, et al. (1980) Effects of clophen A50, 3-methylcholanthrene, pregnenolone-16 alpha-carbonitrile, and phenobarbital on the hepatic microsomal cytochrome P-450-dependent monooxygenase system in rainbow trout, Salmo gairdneri, of different age and sex. Tax Appl Pharm., 54(3): 420-430.
Kawashima T, et al. (2009) Synaptic activity-responsive element int he Arel Arg3. 1 promoter essential for synapse-to-nucleus signaling in activated neurons. PNAS, 106(1): 316-321.

(Continued)

*Primary Examiner* — Svetlana M Ivanova
(74) *Attorney, Agent, or Firm* — Ballard Spahr LLP (57) ABSTRACT

There is disclosed a salt of Formula III, a method for manufacturing thereof as well as uses thereof. (Formula III), wherein X is H or OH, Y is H or a cation selected from the group consisting of Li, Na and K, is a single bond or a double bond, and n is 0.5 or 1.

Formula III

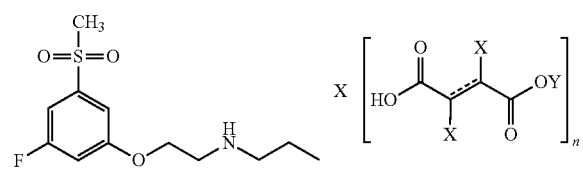

17 Claims, 2 Drawing Sheets

(56) References Cited

OTHER PUBLICATIONS

Link W, et al. (1995) Somatodendritic expression of an immediate early gene is regulated by synaptic activity. Proc Natl Acad Sci USA, 92: 5734-5738.
Lyford GL, et al. (1995) Arc, a Growth Factor and Activity-Regulated Gene, Encodes a Novel Cytoskeleton-Associated Protein That is Enriched in Neuronal Dendrites. Neuron, 14: 433-445.
Moghaddam B, et al. (1989) Ionic composition of microdialysis per/using solution alters the pharmacological responsiveness and basal outflow of striatal dopamine. J. Neurochem., 53: 652-654.
Paxinos G, et al. (1986) The Rat Brain in Stereotaxic Coordinates. NY, Academic Press.
Psychopharmacology 4th Generation of progress, Chapter 68, p. 793-795.
Psychopharmacology 4th Generation of progress, Chapter 101, p. 1205 and 1207.
Psychopharmacology 4th Generation of progress, Chapter 101, p. 1208-1209.
Raubo P, et al. (2006) Aminoalkyl phenyl sulfones—a novel series of 5-HT7 receptor ligands. Bioorganic & Medicinal Chemistry Letters, Pergamon, Elsevier Science, GB, 16(5); 1255-1258.
Remington's Pharmaceutical Sciences. Maack Publishing Co., Easton PA.
Renwick AB, et al. (2001) Metabolism of 2,5-bis(trifluoromethyl)-7-benzyloxy-4-trifluoromethylcoumarin by human hepatic CYP isoforms: evidence for selectivity towards CYP3A4. Xenobiotica, 31(4): 187-204.
Santiago M, et al. (1990) Characterization of the in vivo release of dopamine as recorded by different types of intracerebral microdialysis probes. Naunyn-Schmiedeberg's Arch. Pharmacol., 342: 407-414.
Steward O, et al. (2001) Selective targeting of newly synthesised Arc mRNA to active synapses requires NMDA receptor activation. Neuron, 30: 227-240.
Waters, et al. (1994) Differential effects of dopamine D2 and D3 receptor antagonists in regard to dopamine release, in vivo receptor displacement and behaviour. J. Neural. Transm. Gen. Sect. | 98(1): 39-55.
International Preliminary Report on Patentability issued by the International Bureau on Oct. 22, 2013 for International Application No. PCT/EP2012/056959 filed Apr. 19, 2011 and published as WO 2012/143337 on Oct. 26, 2012.
International Search Report mailed by the International Bureau on Sep. 20, 2012 for International Application No. PCT/EP2012/056959 filed Apr. 19, 2011 and published as WO 2012/143337 on Oct. 26, 2012.
Written Opinion mailed by the International Bureau on Sep. 20, 2012 for International Application No. PCT/EP2012/056959 filed Apr. 19, 2011 and published as WO 2012/143337 on Oct. 26, 2012.
"Age Related Cognitive Decline," http://www.lef.org/protocols/neurologica/age related_cognitive_decline, retrieved on Jul. 21, 2014 (pp. 1-10).
Antipsychotic, http://en.wikipedia.org/wiki/Antipsychotic, retrieved on Jul. 23, 2014 (pp. 1-38).
Chen, et al., "Design, synthesis, and evaluation of potent and selective ligands for the dopamine 3 (D3) receptor with a novel in vivo behavioral profile," Journal of Medicinal Chemistry, 2008, 51, 5950-5908.
Dyhring, T., et al., "The dopaminergic stabilizers pridopidine (ACR16) and(−)-OSU6162 display dopamine D2 receptor antagonism and fast receptor dissociation properties," European Journal of Pharmacology, 2010, 628, 19-26.
Grandy, D., et al., "Cloning of the cDNA and gene for a human D2 dopamine receptor," Proc. Natl. Acad. Sci, USA, Dec. 1989, vol. 86, 9762-9766.
Harig, H. & Pullman, W., "From bench to clinic and back: Perspective on the 1st IQPC translational research conference," Journal of Translational Medicine, 2004, 2, 44.
Iderberg, H., et al., "Animal models of L-DOPA-induced dyskinesia: An update on the current options," Neuroscience, 2012, 211, 13-27.

Kilic, et al., "Effects of dehydroepianodrosterone in amphetamine-induced schizophrenia models in mice," Neuroscience, 2014, 19, 100-105 (Pubmed printout).
Kramer, et al., "The effects of a selective D4 dopamine receptor antagonist (L-745-870) in acutely psychotic inpatients with schizophrenia. D4 dopamine antagonist group," Archives of General Psychiatry, 1997, 54, 567-572 (Pubmed printout).
Lawrence, et al., "The Dl receptor antagonist, SCH23390, induces signs of Parkinsonism in African green monkeys," Life Science, 1991, 40, PL229-234 (Pubmed printout).
Link, W., et al., "Somatodendritic expression of an immediate early gene is regulated by synaptic activity," Proc Natl Acad Sci USA, 1995, 92, 5734-5738.
Lyford, G. L., et al., "Arc, a growth factor and activity-regulated gene, encodes a novel cytoskeleton-associated protein that is enriched in neuronal dendrites," Neuron, 1995, 14, 433-445.
Nemade, R. & Dombeck, M., Symptoms of Substance-Induced Psychotic Disorder, 11 http://sevencounties.org/poc/view_doc.php?type=doc&id=8821&cn=7, retrieved on Jul. 21, 2014 (pp. 1-2).
Ogren, S. O., et al., "The selective dopamine D2 receptor antagonist raclopride discriminates between dopamine-mediated motor function," Psychopharmacology, 1986, 90, 287-294.
Ponten, H., et al., "In vivo pharmacology of the dopaminergic stabilizer pridopidine," European Journal of Pharmacology, 2010, 644, 88-95.
Schafer, S. & Kolkhof, P., "Failure is an option: learning from unsuccessful proof-of-concept trials," Drug Discovery Today, Nov. 2008, vol. 13, No. 21/22, 913-916.
Cenci, M. A. & Lundblad, M., "Utility of 6-Hydroxydopamine lesioned rats in the preclinical screening of novel treatments for Parkinson disease" In: Animal Models of Movement Disorders, LeDoux Mark, Ed., 2005, 193-208.
Berge et al., Journal of Pharmaceutical Sciences, 66:1-19 (1977).
Svensson et al. (2015) ISP—An In vivo based systems pharmacology platform for phenotypic characterization of CNS treatments, translational modelling and drug discovery. Poster presented at the Neuroscience 2015 symposium, Oct. 17-21, 2015 in Chicago, IL USA.
Svensson et al. (2016) ISP—An In vivo based systems pharmacology platform for phenotypic characterization of CNS treatments, translational modelling and drug discovery. Poster presented at the Monitoring Molecules in Neuroscience: 16th International Conference, May 29-Jun. 2, 2016, Gothenburg, Sweden.
Waters et al. (2016) Pharmacology of IRL790, a psychomotor stabilizer for the treatment of L-dopa induced dyskinesias and psychosis in Parkinson's disease. Poster presented at the Dopamine 2016 symposium, Sep. 5-8, 2016 in Vienna, Austria.
Waters et al., ACS Chem. Neurosci., 8:785-797 (2017).
Svenningsson et al., Parkinson's Disease 4:35 (2018).
Svensson et al. (2018) Evolving the Concept of Phenotypic Screening to a New Level of Data-Driven, Systems Oriented Drug Discovery. Oral presentation at the CNS and Neurodegenerative Targets—Discovery on Target conference, Sep. 26-27, 2018, Boston MA USA.
Svensson et al. (2019) ISP—phenotypic screening evolved to a new level of data-driven, systems-oriented drug discovery. Poster presented at the Keystone Symposia, Mar. 3-7, 2019, Breckenridge, CO USA.
Waters et al., J. Pharmacol. Exp. Ther., 374:113-125 (2020) (published online Jun. 18, 2020).
Becanovic et al., J. Pharmacol. Exp. Ther., 374:126-133 (2020) (published online Jun. 18, 2020).
Sjoberg et al., Pharmacol. Res. Perspect., 9:e00792 (2021) (First published May 20, 2021).
Svenningsson et al. (2021) Mesdopetam suppresses sensitization and AIMs in the rodent unilateral 6-OHDA lesion model of Parkinson's disease. Poster presented at the Society for Neuroscience Global Connectome: A virtual event on Jan. 11, 2021.
Alshimemeri et al., Expert Opinion on Emerging Drugs, 25:131-144 (2020) (Accepted author version posted online May 4, 2020).
Becanovic et al., JPET Fast Forward, DOI: 10.1124/jpet.119. 264754 (2020) (Published online May 1, 2020).

(56) References Cited

OTHER PUBLICATIONS

Waters et al., JPET Fast Forward, DOI: 10.1124/jpet.119.264226 (2020) (Published online May 1, 2020).

* cited by examiner

PHARMACEUTICALLY ACCEPTABLE SALTS OF [2-(3-FLUORO-5-METHANE-SULFONYL-PHENOXY)ETHYL](PROPYL)AMINE AND USES THEREOF

TECHNICAL FIELD

The present disclosure concerns pharmaceutically acceptable salts of the compound [2-(3-fluoro-5-methanesulfonylphenoxy)ethyl](propyl)amine. More specifically, the present disclosure concerns a tartaric acid salt of [2-(3-fluoro-5-methanesulfonylphenoxy)ethyl](propyl)amine and a fumaric acid salt of [2-(3-fluoro-5-methanesulfonylphenoxy)ethyl](propyl)amine, respectively. The present disclosure also concerns a method for preparation of the aforementioned salts as well as uses of the aforementioned salts.

BACKGROUND

WO 2012/143337 discloses phenoxy-ethyl-amine derivatives useful as modulators of cortical and basal ganglia dopaminergic and N-methyl-D-aspartate (NMDA) receptor mediated glutamatergic neurotransmission, and more specifically for the treatment of diseases that are responsive to modulation of dopaminergic and glutamatergic function in the central nervous system. The compound [2-(3-fluoro-5-methanesulfonylphenoxy)-ethyl](propyl)amine is disclosed in its non-salt form as well as in the form of a hydrochloric acid salt in Example 1. It is stated that said hydrochloric acid salt has a melting point of 191° C.

The compound 2-(3-fluoro-5-methanesulfonylphenoxy)ethyl](propyl)amine is currently in clinical development for the treatment of dyskinesia in Parkinson's disease, i.e. involuntary movements that often follow after a number of years of treatment with L-dopa, and for the treatment of psychosis in Parkinson's disease.

The further investigation and development of 2-(3-fluoro-5-methanesulfonylphenoxy)-ethyl](propyl)amine has revealed a need for a form of [2-(3-fluoro-5-methanesulfonylphenoxy)ethyl](propyl)amine exhibiting satisfactory pharmaceutical properties as well as satisfactory handling and drug properties, in particular on an industrial scale.

SUMMARY

It is an object of the present disclosure to provide a form of [2-(3-fluoro-5-methane-sulfonylphenoxy)ethyl](propyl)amine that exhibits satisfactory pharmaceutical properties as well as handling and drug properties.

The present disclosure provides a salt of Formula III:

Formula III said salt being a combination of a compound of Formula I and an acid of Formula II:

Formula I

Formula II in a ratio of 1:n,
wherein
X is H or OH,
Y is H or a cation selected from the group consisting of Li, Na and K,
--- is a single bond or a double bond, and
n is 0.5 or 1.

The present disclosure also provides a pharmaceutical composition comprising a salt of Formula III as described herein in admixture with a pharmaceutically acceptable excipient, carrier and/or diluent.

The present disclosure also provides a salt of Formula III as described herein for use as a medicament in therapy.

The present disclosure also provides a salt of Formula III as described herein for use in the treatment and/or prevention of a disease, disorder and/or condition which is at least one of the following: psychosis, schizophrenia, schizophreniform disorder, bipolar disorder, psychotic disorder, drug induced psychotic disorder, mood disorder, anxiety disorder, depression, obsessive-compulsive disease, dementia, age-related cognitive impairment, Autism spectrum disorders, ADHD, cerebral Palsy, Gilles de la Tourette's syndrome, brain injury, sleep disorder, sexual disorder, eating disorder, obesity, headache, pains in conditions characterized by increased muscular tone, Parkinson's disease, parkinsonian syndrome, dyskinesia, L-DOPA induced dyskinesias, Tardive dyskinesias, dystonia, tics and tremor dementia, Huntington's disease, movement disorder induced by drugs, restless legs, narcolepsy, Alzheimer's disease and disorder(s) related to Alzheimer's disease.

The present disclosure also provides use of a salt of Formula III as described herein for the manufacture of a medicament for use in the treatment and/or prevention of a disease, disorder and/or condition which is at least one of the following: psychosis, schizophrenia, schizophreniform disorder, bipolar disorder, psychotic disorder, drug induced psychotic disorder, mood disorder, anxiety disorder, depression, obsessive-compulsive disease, dementia, age-related cognitive impairment, Autism spectrum disorders, ADHD, cerebral Palsy, Gilles de la Tourette's syndrome, brain injury, sleep disorder, sexual disorder, eating disorder, obesity, headache, pains in conditions characterized by increased muscular tone, Parkinson's disease, parkinsonian syndrome, dyskinesia, L-DOPA induced dyskinesias, Tardive dyskinesias, dystonia, tics and tremor dementia, Huntington's disease, movement disorder induced by drugs, restless legs, narcolepsy, Alzheimer's disease and disorder(s) related to Alzheimer's disease.

The present disclosure also provides a method for treatment and/or prevention of a disease, disorder and/or condition which is at least one of the following: psychosis, schizophrenia, schizophreniform disorder, bipolar disorder, psychotic disorder, drug induced psychotic disorder, mood disorder, anxiety disorder, depression, obsessive-compulsive disease, dementia, age-related cognitive impairment, Autism spectrum disorders, ADHD, cerebral Palsy, Gilles de la Tourette's syndrome, brain injury, sleep disorder, sexual disorder, eating disorder, obesity, headache, pains in conditions characterized by increased muscular tone, Parkinson's disease, parkinsonian syndrome, dyskinesia, L-DOPA induced dyskinesias, Tardive dyskinesias, dystonia, tics and tremor dementia, Huntington's disease, movement disorder induced by drugs, restless legs, narcolepsy, Alzheimer's disease and disorder(s) related to Alzheimer's disease; comprising administering to a mammal, such as a human or an animal, in need thereof, an effective amount of a salt of Formula III as described herein.

The present disclosure also provides a method for preparing a salt of Formula III as described herein said method comprising the steps of:
providing a compound of Formula I, as described herein, and an acid of Formula II, as described herein, in a ratio of 1:0.5 or 1:1,
combining said compound of Formula I with said acid of Formula II in a solvent to form a solution, and
allowing said solution to stand until a precipitate forms, and
isolating said precipitate by filtration thereby providing the salt of Formula III.

DESCRIPTION

The present disclosure provides a salt of Formula III:

Formula III said salt being a combination of a compound of Formula I and an acid of Formula II:

Formula I

Formula II in a ratio of 1:n,
wherein
X is H or OH,
Y is H or a cation selected from the group consisting of Li, Na and K,
--- is a single bond or a double bond, and
n is 0.5 or 1.

It will be appreciated that the acid of Formula II described herein may be represented as.

For example, when Y is H, i.e. hydrogen; the acid of Formula II may be represented as In a further example, when Y is Na, i.e. sodium, the acid of Formula II may be represented as Further values of X, Y, --- and n will now follow. It will be appreciated that such values may be used with any of the definitions, examples and/or claims described herein.

For instance, when
X is OH,
Y is H, and
--- is a single bond,
the acid of Formula II is tartaric acid such as L-(+)-tartaric acid and/or D-(−)-tartaric acid.

The tartaric acid may be combined with the compound of Formula I as described herein.

Thus, for the salt of Formula III when
X is OH,
Y is H, and
--- is a single bond, there is provided a salt of Formula IV being a combination of a compound of Formula I and tartaric acid:

Formula IV

X $_n$.

The tartaric acid described herein may be L-(+)-tartaric acid and/or D-(−)-tartaric acid. For instance, the tartaric acid may be L-(+)-tartaric acid. In a further example, the tartaric acid may be D-(−)-tartaric acid. In still a further example, the tartaric acid may be a mixture such as a racemic mixture of L-(+)-tartaric acid and D-(−)-tartaric acid.

The ratio of the compound of Formula I and the tartaric acid may be 1:n, i.e. the ratio of the compound of Formula I to the tartaric acid, wherein n is a number such as 0.5 or 1.

For instance, when the ratio of the compound of Formula I to the tartaric acid is 1:0.5 there is provided a salt of Formula IVa. In a further example, when the ratio of the compound of Formula I to the tartaric acid is 1:1 there is provided a salt of Formula IVb.

Formula IVa

$_{0.5}$

Formula IVb

X .

In a further example, when
X is H,
Y is H, and
--- is a double bond,
the acid of Formula II is fumaric acid. The fumaric acid may be combined with the compound of Formula I as described herein.
Thus, for the salt of Formula III when
X is H,
Y is H, and
--- is a double bond,
there is provided a salt of Formula V being a combination of a compound of Formula I and fumaric acid:

Formula V $_n$.

The ratio of the compound of Formula I and the fumaric acid may be 1:n, wherein n is a number such as 0.5 or 1. For example, n may be 0.5. In a further example, n may be 1.

For instance, when the ratio of the compound of Formula I to the fumaric acid is 1:0.5 there is provided a salt of Formula Va. In a further example, when the ratio of the compound of Formula I to the fumaric acid is 1:1 there is provided a salt of Formula Vb.

Formula Va

X $_{0.5}$

Formula Vb

X .

There is also provided a salt of Formula III as described herein such as a salt of Formula IV or a salt of Formula V, wherein one or more of the hydrogen atoms of the compound of Formula I is/are replaced with deuterium. Additionally or alternatively, the salt of Formula III may be labelled with isotopes other than deuterium as described herein.

The salt of Formula III as described herein is pharmaceutically acceptable and has unexpectedly been found to exhibit properties of high crystallinity (i.e. being substantially crystalline), not being hygroscopic, exhibiting high melting point and/or satisfactory water solubility. Furthermore, the salt of Formula III may be isolated in good chemical yield with a high purity.

There is provided a salt of Formula III, as described herein, characterized by being crystalline. The crystallinity may be determined by XRPD or any other appropriate method known in the art. The high crystallinity of the salt of Formula III makes it well-defined with respect to, for instance, melting point and XRPD. This is a benefit in making tablets and is believed to enhance storage stability. In this document, high crystallinity intends a degree of crystallinity of about 80% or more such as about 85%, about 90%, about 95%, about 99% or about 100% as measured by XRPD or any other appropriate method of measurement known in the art.

Figure 1:
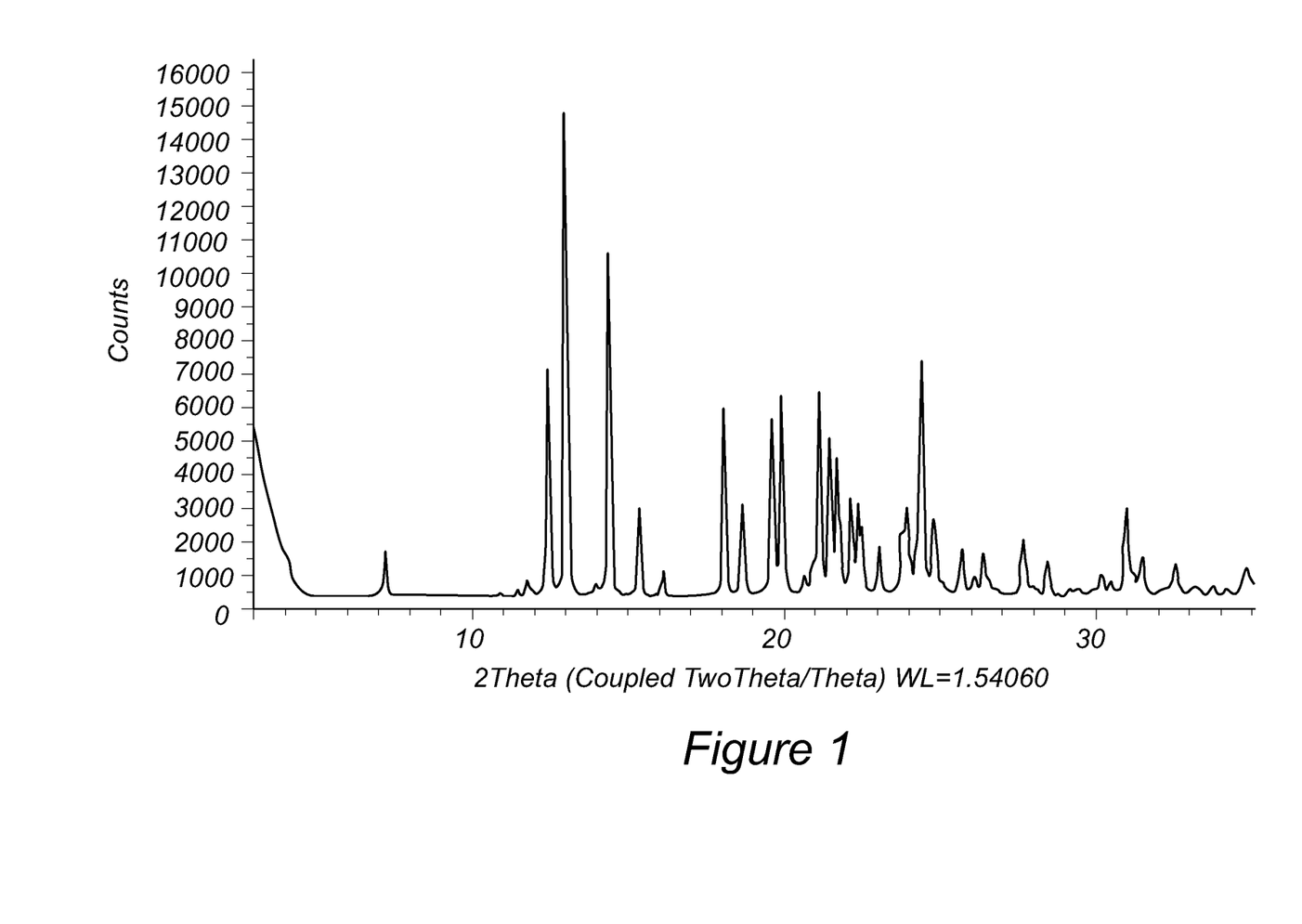
FIG. 1 shows an XRP diffractogram of the salt of Formula IVa.
Figure 2:
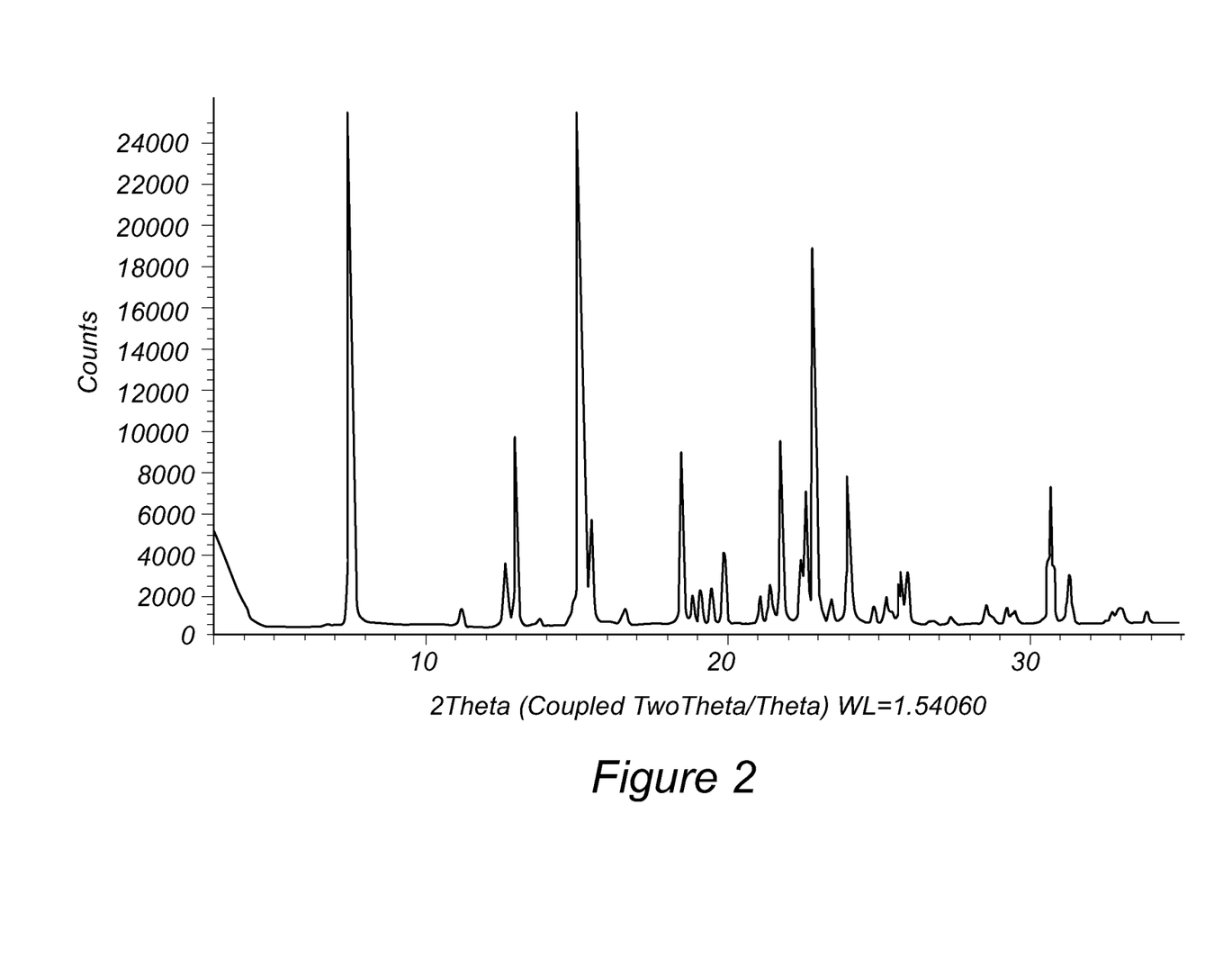
FIG. 2 shows an XRP diffractogram of the salt of Formula Va.

The salt of Formula III, as described herein, may be characterized by an XRP diffractogram as shown in FIG. 1 or in FIG. 2. The salt of Formula III such as the salt of Formula IVa may be characterized by an XRP diffractogram comprising a peak at about 13.02 2θ such as 13.0 2θ, and optionally at least one further peak selected from the following: about 12.43 such as about 12.4, about 14.40 such as about 14.4, about 21.10 such as about 21.1, about 24.36 such as about 24.4 2θ. The salt of Formula IVa may also be characterized by an XRP diffractogram comprising a peak at about 12.43, about 13.02, about 14.40, about 21.10, about 24.36 2θ, and optionally at least one further peak selected from the following: about 18.07, about 19.92 2θ. For instance, the XRP diffractogram may comprise peaks at about 12.4, about 13.0, about 14.4, about 21.1 and about 24.4 2θ. The salt of Formula IVa may also be characterized by an XRP diffractogram comprising a peak at about 12.43, about 13.02, about 14.40, about 18.07, about 19.92, about 21.10, about 24.36 2θ, and optionally at least one further peak selected from the following: about 19.62, about 21.44 2θ. Further, the salt of Formula III such as the salt of Formula Va may be characterized by an XRP diffractogram comprising a peak at about 15.27 2θ, and optionally at least one further peak selected from the following: about 7.62 such as about 7.6, about 12.98 such as about 13.0, about 21.84 such as about 21.8, about 22.98 such as about 23.0 2θ. The salt of Formula Va may also be characterized by an XRP diffractogram comprising a peak at about 7.62, about 12.98, about 15.27, about 21.84, about 22.98 2θ, and optionally at least one further peak selected from the following: about 18.55, about 24.08 2θ. For instance, the XRP diffractogram may comprise peaks at about 7.6, about 13.0, about 15.3, about 21.8 and about 23.0 2θ. The salt of Formula Va may also be characterized by an XRP diffractogram comprising a peak at about 7.62, about 12.98, about 15.27, about 18.55, about 21.84, about 22.98, about 24.08 2θ, and optionally at least one further peak selected from the following: about 22.65, about 30.79 2θ.

The salt of Formula III such as the salt of Formula IV and the salt of Formula V has been found to have a high melting point and a satisfactory water solubility. The high melting point of the salt of Formula III is a benefit in, for instance, tablet making. The satisfactory water solubility of the salt of Formula III makes it suitable for any administration to a human, such as oral administration. The salt of Formula IVa has been found to have a melting point of about 187.6° C. Further, the water solubility of the salt of Formula IVa has been found to be about 185 mg/mL. The salt of Formula Va has been found to have a melting point of about 184.9° C. Further, the water solubility of the salt of Formula Va has been found to be about 92 mg/mL. The melting point and/or water solubility may be determined as described in the Examples section of this document.

Furthermore, the salt of Formula IV has been found to not being hygroscopic at any tested relative humidity and that is advantageous since it allows for storage without being changed by surrounding humidity. It has been found that the salt of Formula IV changes its weight by ±0.3% by weight or less at any humidity such as any relative humidity as described herein, i.e. it is not hygroscopic or substantially not hygroscopic. In an example, the salt of Formula IV does not change its weight at any humidity such as any tested relative humidity.

There is also provided a pharmaceutical composition comprising:

a salt of Formula III as described herein such as a salt of Formula IV or a salt of Formula V in admixture with a pharmaceutically acceptable excipient, carrier and/or diluent. The pharmaceutical composition may be provided in a single dosage form such a tablet, pill, capsule or the like. The amount of the compound of Formula I of the salt of Formula III in the single dosage form may vary. For instance, the amount of the compound of Formula I of said salt may be from about 2.0 mg up to about 10.0 mg such as about 2.5 mg to about 7.5 mg. Further, the amount of the compound of Formula I of said salt may be about 5.0 mg, about 7.5 mg or about 2.5 mg.

Surprisingly, it has been found that administration of the aforementioned amounts to a patient such as a human reduces symptoms associated with a disease, disorder or condition as described herein, in particular L-DOPA induced dyskinesias, to a greater extent as compared to administration of the compound of Formula I of the salt of Formula III in a higher amount such as an amount equal to or above 10 mg. Thus, administration of a lower amount is more advantageous than administration of a higher amount.

Further, there is provided a salt of Formula III as described herein such as a salt of Formula IV or a salt of Formula V for use as a medicament.

Further, there is provided a salt of Formula III as described herein such as a salt of Formula IV or a salt of Formula V, or a pharmaceutical composition as described herein, for use in the treatment and/or prevention of a disease, disorder and/or condition which is at least one of the following: psychosis, schizophrenia, schizophreniform disorder, bipolar disorder, psychotic disorder, drug induced psychotic disorder, mood disorder, anxiety disorder, depression, obsessive-compulsive disease, dementia, age-related cognitive impairment, Autism spectrum disorders, ADHD, cerebral Palsy, Gilles de la Tourette's syndrome, brain injury, sleep disorder, sexual disorder, eating disorder, obesita, headache, pains in conditions characterized by increased muscular tone, Parkinson's disease, parkinsonian syndrome, dyskinesia, L-DOPA induced dyskinesias, Tardive dyskinesias, dystonia, tics and tremor dementia, Huntington's disease, movement disorder induced by drugs, restless legs, narcolepsy, Alzheimer's disease and disorder(s) related to Alzheimer's disease.

Further, there is provided a salt of Formula III as described herein such as a salt of Formula IV or a salt of Formula V, or a pharmaceutical composition as described herein, for use in the treatment and/or prevention of a disease, disorder and/or condition which is schizophrenia, L-DOPA induced dyskinesias and/or Huntington's disease. Moreover, there is provided a salt of Formula III as described herein, or a pharmaceutical composition as described herein, such as a salt of Formula IV or a salt of Formula V for use in the treatment and/or prevention of a disease, disorder and/or condition which is L-DOPA induced dyskinesias.

There is also provided a salt of Formula III for use as described herein or a pharmaceutical composition for use as described herein, wherein the salt or the pharmaceutical composition is administered to a patient such as a human in a dosage from about 2.0 mg up to about 10.0 mg such as about 2.5 mg, about 5.0 mg or about 7.5 mg. As a result, the disease, disorder and/or condition, or symptoms associated with said disease, disorder and/or condition, is/are alleviated or reduced to a greater extent as compared to administration of the salt or the pharmaceutical composition to a patient in a dosage equal to or greater than 10 mg. The administration in a dosage equal to or greater than about 10 mg and the administration to provide the dosage from about 2.0 mg up to about 10.0 mg may take place an equal number of times, such as an equal number of times daily, such as twice daily.

As used herein, the expression "from . . . up to . . . " intends "from . . . up to but not including . . . ". For instance, the expression "from 2.0 mg up to 10.0 mg" intends "from 2.0 mg up to but not including 10.0 mg". In the latter case, the amount 9.99 mg is included while the amount 10.0 mg is not included.

There is also provided use of a salt of Formula III as described herein such as a salt of Formula IV or a salt of Formula V, or a pharmaceutical composition as described herein, for the manufacture of a medicament for use in the treatment and/or prevention of a disease, disorder and/or condition which is at least one of the following: psychosis, schizophrenia, schizophreniform disorder, bipolar disorder, psychotic disorder, drug induced psychotic disorder, mood disorder, anxiety disorder, depression, obsessive-compulsive disease, dementia, age-related cognitive impairment, Autism spectrum disorders, ADHD, cerebral Palsy, Gilles de la Tourette's syndrome, brain injury, sleep disorder, sexual disorder, eating disorder, obesity, headache, pains in conditions characterized by increased muscular tone, Parkinson's disease, parkinsonian syndrome, dyskinesia, L-DOPA induced dyskinesias, Tardive dyskinesias, dystonia, tics and tremor dementia, Huntington's disease, movement disorder induced by drugs, restless legs, narcolepsy, Alzheimer's disease and disorder(s) related to Alzheimer's disease.

Further, there is provided use of a salt of Formula III as described herein such as a salt of Formula IV or a salt of Formula V, or a pharmaceutical composition as described herein, for the manufacture of a medicament for use in the treatment and/or prevention of a disease, disorder and/or condition which is schizophrenia, L-DOPA induced dyskinesias and/or Huntington's disease. Moreover, there is provided a use of a salt of Formula III as described herein such as a salt of Formula IV or a salt of Formula V, or a pharmaceutical composition as described herein, for the manufacture of a medicament for use in the treatment and/or prevention of a disease, disorder and/or condition which is L-DOPA induced dyskinesias.

There is also proved a use of use of a salt of Formula III as described herein, or a pharmaceutical composition as described herein, wherein the salt or the pharmaceutical composition is administered to a patient such as a human in a dosage from about 2.0 mg up to about 10.0 mg such as about 2.5 mg, about 5.0 mg or about 7.5 mg. As a result, the disease, disorder and/or condition, or symptoms associated with said disease, disorder and/or condition, is/are alleviated or reduced to a greater extent as compared to administration of the salt or the pharmaceutical composition to a patient in a dosage equal to or greater than 10 mg. The administration to provide the dosage equal to or greater than about 10 mg and the administration to provide the dosage from about 2.0 mg up to about 10.0 mg may take place an equal number of times, such as an equal number of times daily, such as twice daily.

There is also provided a method for treatment and/or prevention of a disease, disorder and/or condition which is at least one of the following: psychosis, schizophrenia, schizophreniform disorder, bipolar disorder, psychotic disorder, drug induced psychotic disorder, mood disorder, anxiety disorder, depression, obsessive-compulsive disease, dementia, age-related cognitive impairment, Autism spectrum disorders, ADHD, cerebral Palsy, Gilles de la Tourette's syndrome, brain injury, sleep disorder, sexual disorder, eating disorder, obesity, headache, pains in conditions characterized by increased muscular tone, Parkinson's disease, parkinsonian syndrome, dyskinesia, L-DOPA induced dyskinesias, Tardive dyskinesias, dystonia, tics and tremor dementia, Huntington's disease, movement disorder induced by drugs, restless legs, narcolepsy, Alzheimer's disease and disorder(s) related to Alzheimer's disease; comprising administering to a patient, such as a mammal, human or an animal, in need thereof, an effective amount of a salt of Formula III as described herein, such as a salt of Formula IV or a salt of Formula V, or a pharmaceutical composition as described herein.

There is also provided a method for treatment and/or prevention of a disease, disorder and/or condition which is schizophrenia, L-DOPA induced dyskinesias and/or Huntington's disease; comprising administering to a patient, such as a mammal, human or an animal, in need thereof, an effective amount of a salt of Formula III as described herein, such as a salt of Formula IV or a salt of Formula V, or a pharmaceutical composition as described herein. Moreover, there is provided a method for treatment and/or prevention of a disease, disorder and/or condition which is L-DOPA induced dyskinesias comprising administering to a patient, such as a mammal, human or an animal, in need thereof, an effective amount of the salt of Formula III as described herein, such as a salt of Formula IV or a salt of Formula V, or a pharmaceutical composition as described herein.

In the method for treatment and/or prevention described herein, the effective amount of the salt of Formula III or the pharmaceutical composition may involve administration of a dosage from about 2.0 mg up to about 10.0 mg such as about 2.5 mg, about 5.0 mg or about 7.5 mg. As a result, the disease, disorder and/or condition, or symptoms associated with said disease, disorder and/or condition, is/are alleviated or reduced to a greater extent as compared to administration of the salt or the pharmaceutical composition to a patient to provide the compound of Formula I in a dosage equal to or greater than 10 mg. The administration to provide the dosage in an amount equal to or greater than about 10 mg and the administration to provide the dosage from about 2.0 mg up to about 10.0 mg may take place an equal number of times, such as an equal number of times daily, such as twice daily.

It will be appreciated that the dosage described herein such as a dosage from about 2.0 mg to about 10.0 mg of the salt of Formula III or the pharmaceutical composition described herein intends the dosage calculation based on the compound of Formula I, i.e. the compound of Formula I in non-salt form. For example, when the dosage is 7.5 mg this means that an amount of 7.5 mg of the compound of Formula I is provided.

The salt of Formula III may be prepared by combining a compound of Formula I as described herein with an acid of Formula II as described herein. The compound of Formula I may be prepared as described herein, as described in WO 2012/143337 and/or using methods known in the art.

Accordingly, the present disclosure also provides a method for preparing a salt of Formula III as described herein such as a salt of Formula IV or a salt of Formula V said method comprising the steps of:
providing a compound of Formula I as described herein and an acid of Formula II as described herein in a ratio of 1:n such as a ratio of 1:0.5 or 1:1,
combining said compound of Formula I with said acid of Formula II in a solvent to form a solution, and
allowing said solution to stand until a precipitate forms, and
isolating said precipitate by filtration thereby providing the salt of Formula III.

In the method for preparing a salt of Formula III as described herein, the ratio of the compound of Formula I to the acid of Formula II may be 1:0.5 or 1:1. Further, the solvent may be a single solvent or a mixture of solvents. The solvent or mixture of solvents may comprise or consist of organic solvent(s) such as ethanol. Further, the step of forming a precipitate may be performed at room temperature. In this document, room temperature intends a temperature within the range of from about 20° C. to about 25° C., such as from about 20° C. to about 22° C. The acid of Formula II may be tartaric acid or fumaric acid.

Salts

In this document, the chemical structure of the salt of Formula III comprising a combination of the compound of Formula I and an acid of Formula II has been drawn as a complex wherein the acidic proton(s) of the acid is attached to said acid. However, the skilled person understands that the acidic proton(s) of the acid of Formula II may be attached to the nitrogen atom of the compound of Formula I and/or shared between the nitrogen atom of the compound of Formula I and the acid of Formula II, and this is also intended to be encompassed by the complexes/salts described herein. For instance, the salt of Formula III being a 1:1 combination of the compound of Formula I and the acid of Formula II may also be represented as:

Formula III

It will be appreciated that the salts of Formula III described herein may be converted to another salt of Formula III using standard procedures known in the art.

Isotopes

The compound of Formula I of the salt of Formula III of the present disclosure may contain an atomic isotope at one or more of the atoms that constitute said compounds, i.e. said compound may be labelled with an isotope. For example, the compound of Formula I may be labelled with one or more isotopes, such as for example tritium ($^3H$), deuterium ($^2H$), iodine-125 ($^{125}I$) or carbon-14 ($^{14}C$). In an example, the compound is labelled with one or more deuterium atoms. All isotopic variations of the compounds of the present disclosure, whether radioactive or not, are intended to be encompassed within the scope of the present disclosure.

Thus, the present disclosure provides a compound as described herein, such as a compound of Formula I, which is labelled with one or more isotopes such as deuterium. The compounds labelled with an isotope as described herein may be combined with an acid as described herein thereby providing a salt as described herein.

The disclosure is further illustrated by the following non-limitative Examples.

EXAMPLES

In this document, unless otherwise stated, the drawing of the chemical compounds have been made using the software package Chem Doodle, ver. 9.0.3. The naming of compounds was made using the program MarvinSketch 16.10.17.0. If the drawing and chemical name are inconsistent, the chemical structure shall be considered to be correct.

General

Reagents and solvents were used as purchased without purification.

HPLC analyses were performed on a Dionex HPLC Module with Dionex UVD 170 U Detector and a Thermo Finnigan MS. Column: Waters XBridge™ 018, 4.6×50 mm, Mobile phase A: 0.1% formic acid (aq.), Mobile phase B: acetonitrile, Flow: 1 mL/min, Injection volume: 3-20 µL, Detection: 220-320 nm, Gradient: 0% to 100% B in 5 min, buffers A or C were used.

NMR analyses were performed on a Varian Mercury 400 instrument operating at 400 MHz. Residual solvent peak was used as an internal standard.

The assay and purity determination of the compounds were performed by gradient liquid chromatography with UV-detection at 260 nm. That means that a specific volume of the solution was evaporated and the residue was analysed by chromatography and compared with that of a chromatogram of a known amount of said intermediate.

Column: Hypersil Gold C18, 4.6×150 mm, 3 µm (Thermo), Column temperature: 40° C., Column oven: Dionex TCC-3000 SD, Pump: Dionex LPG-3400 SD, Flow rate: 1 mL/min, Injector: Dionex WPS-3000 SL, Injection volume: 10 µL, Detector: Dionex DAD-3000, Wavelength: 260 nm, Data collecting system: Chromeleon.

XRPD data were collected on a Bruker D8 Advance (2005) instrument. Radiation Copper Ka, λ=1.54180 Å, Kb filter 0.020 mm Ni foil, Anode voltage: 40 kV, Anode current 40 mA, Detector: LynxEye (1D-position sensitive), Slits 0.6 mm and 8 mm, Step size 0.02°, Scan speed 0.2 s/step, Interval (2Θ) (3-35)° in 2θ scale.

Regular Water Solubility Test

Water solubility tests for the salts as described herein were performed as follows unless otherwise stated. 0.05 g of each salt was weighed in a flask and the mass of flask+salt (m-vs) was recorded. Water was slowly added dropwise into the flask with salt until full dissolution was achieved as observed by the naked eye. The mass of flask+salt+solvent (m-svs) was recorded. The solubility expressed as "grams of solute/kg of solvent", i.e. "grams of salt/kg of solvent", was calculated according to the equation:

$$\text{Solubility} = \frac{(s) \times 1000}{(m-svs)-(m-vs)} \quad \text{Eq. 1}$$

In Eq. 1:
(s) stands for the weight of the salt measured in kg,
(m-svs) stands for the mass of the flask+salt+solvent measured in kg, and
(m-vs) stands for the mass of the flask+salt measured in kg.

The value of (s) was 0.05/1000 kg.

Since the solubility was measured in water, and water has a density of 1 g/mL the unit of the solubility may be g/L or mg/mL.

Flask Method Water Solubility Test

In some cases, a further water solubility test (Flask method water solubility test) was performed as follows. An excess of salt was added to water. The mixture was equilibrated (shaking) for at least 24 hours thereby providing a saturated salt solution. Then the saturated solution was clear-filtered and transferred into a clean pre-weighed flask (mv). The mass of flask+saturated solution (mvs) was recorded. The solvent was evaporated under reduced pressure until constant mass. Flask containing dried residue was weighed (mvdr). The solubility expressed as "grams of solute/kg of solvent", i.e. "grams of salt/kg of solvent", was calculated according to the equation:

$$\text{Solubility} = \frac{(mvdr - mv) \times 1000}{(mvs - mvdr)} \quad \text{Eq. 2}$$

In Eq. 2:
(mvdr-mv) is the weight difference in kg between (i) the mass of the flask containing dried residue after evaporation of the solvent and (ii) the mass of the flask, and
(mvs-mvdr) is the weight difference in kg between (i) the mass of the flask including the saturated salt solution and (ii) the mass of the flask containing the dried residue. Since the solubility was measured in water, and water has a density of 1 g/mL the unit of the solubility may be g/L or mg/mL.

Hygroscopicity Tests

Hygroscopicity test of the L-tartaric salt of [2-(3-fluoro-5-methanesulfonylphenoxy)-ethyl](propyl)amine was performed by keeping exact weight samples of the salt at varied humidity at 30° C. After one week, the samples were weighed again and based on the original weight the percentage weight difference was calculated.

Hygroscopicity test of the hydrochloric acid salt of [2-(3-fluoro-5-methanesulfonyl-phenoxy)ethyl](propyl)amine was recorded on a TA instrument Q550000SA. The temperature was 25° C. using step intervals of 10% between 0% and 95% RH in two consecutive cycles.

Abbreviations g gram(s)
mg milligram(s)
HCl Hydrochloric acid
EtOH Ethanol
HPLC High Performance Liquid Chromatography
M molar, i.e. mole(s)/liter
MTBE Methyl tert-butyl ether
min. minute(s)
mg milligram(s)
mL millilitre
mol mole
mmol(e) millimole
MS Mass Spectrometry
nM nanoMolar
NMR Nuclear Magnetic Resonance
i-PrOAc Isopropyl acetate
THF Tetrahydrofurane
XRP X-Ray Powder
XRPD X Ray Powder Diffraction
UV ultraviolet
A Angstrom
DVS Dynamic Vapor Sorption
RH Relative Humidity
b.i.d. Twice (two times) a day
TA Thermal Analysis Example 1

Synthesis of 2-(3-fluoro-5-methanesulfonylphenoxy)-N-propylacetamide

To a solution of 3-fluoro-5-methanesulfonylphenol (see WO 2006/137790; 20.6 g, 152 mmol) in i-PrOAc (290 mL) was added 2-chloro-N-propylacetamide (29.0 g, 152 mmol) followed by potassium carbonate (42.0 g, 304 mmol). The reaction mixture was heated to reflux temperature and stirred at this temperature for 20 h. The mixture was cooled to room temperature and then water (320 mL) was added. The formed slurry was stirred for 2 h and the precipitate was isolated by filtration. The filter cake was washed with water (2×115 mL) and then with ethanol (3×90 mL). The product was dried by pulling air through it for 4 h. There was obtained 40.0 g (91%) of 2-(3-fluoro-5-methanesulfonylphenoxy)-N-propylacetamide as a solid with a purity of >99 area % (HPLC). $^1$H NMR (400 MHz, DMSO-d$_6$): δ 0.83 (t, 3H), 1.45 (m, 2H), 3.09 (m, 2H), 3.26 (s, 3H), 4.63 (s, 2H), 7.23 (m, 1H), 7.38 (m, 2H), 8.20 (m, 1H).

Example 2

Synthesis of [2-(3-fluoro-5-methanesulfonylphenoxy)ethyl](propyl)amine

A mixture of 2-(3-fluoro-5-methanesulfonylphenoxy)-N-propylacetamide (39.0 g, 135 mmol) and THF (390 mL) was heated to 35° C. and 1M solution of $BH_3 \cdot THF$ complex in THF (277 mL, 277 mmol) was added over 1 h. The mixture was stirred at 35° C. for 4 h, then at room temperature overnight and then cooled to 7° C. Water (195 mL) was slowly added followed by 37% HCl (6.3 mL, 200 mmol) and the mixture was heated to 56° C. for 3.5 h. Additional amount of water (40 mL) was added followed by 37% HCl (2.5 mL) and the stirring was continued for 28 h at 56° C. After allowing the mixture to cool to room temperature, it was diluted with water (195 mL) and then washed with MTBE (2×200 mL). The pH was adjusted to 11.1 by adding an aqueous solution of NaOH (50%) and then the mixture was extracted with MTBE (2×215 mL). The organic solutions were washed with water (2×120 mL) and then concentrated under reduced pressure until the remaining volume was 60 mL. EtOH (120 mL) was added and the distillation continued until the volume left was approximately 60 mL. The co-evaporation with EtOH was repeated twice and finally the evaporation continued until the remaining volume was approximately 60 mL. The desired [2-(3-fluoro-5-methanesulfonylphenoxy)ethyl]-(propyl)amine was obtained as an EtOH-solution (1.5 M) with a purity of >99 area % (HPLC) and the yield (66%) was determined by using an aliquot evaporation method. $^1$H NMR (400 MHz, $CDCl_3$): δ 0.95 (t, 3H), 1.56 (m, 2H), 2.67 (t, 2H), 3.04 (m, 2H), 3.06 (s, 3H), 4.14 (t, 2H), 6.90 (m, 1H), 7.2-7.3 (m, 2H).

Example 3

Synthesis of [2-(3-fluoro-5-methanesulfonylphenoxy)ethyl](propyl)amine Hemi-L-Tartrate The EtOH-solution of [2-(3-fluoro-5-methanesulfonylphenoxy)ethyl](propyl)amine from Example 2 (estimated amount: 24.5 g, 88.9 mmol) was diluted with EtOH until the concentration was 0.40 M. A solution of L-tartaric acid (6.81 g, 45.4 mmol) in water (20 mL) was added. The formed slurry was heated to reflux temperature and additional amounts of EtOH (50 mL) and water (5 mL) were added. The heating was continued until all solids dissolved. After allowing the mixture to cool to room temperature, the formed slurry was stirred at room temperature overnight, and then at 5 to 10° C. for 5 h. The precipitate was isolated by filtration and the filter cake was washed with EtOH (3×35 mL). The product was dried by pulling air through it for 20 min. There was obtained 29.9 g (96%) of [2-(3-fluoro-5-methanesulfonylphenoxy)ethyl](propyl)amine hemi-L-tartrate as a solid with an LC-purity of 99.9%. $^1$H NMR (400 MHz, DMSO-$d_6$): δ 0.89 (t, 3H), 1.55 (m, 2H), 2.74 (t, 2H), 3.13 (t, 2H), 3.28 (s, 3H), 3.89 (s, 1H), 4.27 (t, 2H), 7.25 (m, 1H), 7.3-7.4 (m, 2H).

X-ray powder diffraction analysis was performed on a sample of the crystals of the hemi-L-tartrate salt of [2-(3-fluoro-5-methanesulfonylphenoxy)ethyl](propyl)amine as prepared above according to standard methods using the instrument, equipment and the conditions described in the general description. The analysis provided the diffractogram depicted in FIG. 1. The main characteristic peaks, with positions and relative intensities, have been extracted from the diffractogram in FIG. 1 and is given below in Table 1.

It will be understood that the relative intensities of peaks may vary according to the orientation of the sample under test and on the type and setting of the instrument used so that the intensities in the XRD traces included herein are illustrative and not intended to be used for absolute comparison.

TABLE 1

Positions and intensities of the major peaks in the XRP-diffractogram of the salt of Formula IVa which is a combination of the compound of Formula I and L-(+)-tartaric acid in a ratio of 1:0.5.

| Angle 2θ/° | d-value/Å | % Relative intensity |
|---|---|---|
| 7.18 | 12.3 | 9 |
| 11.44 | 7.73 | 1 |
| 11.78 | 7.51 | 3 |
| 12.43 | 7.11 | 49 |
| 13.02 | 6.79 | 100 |
| 13.94 | 6.35 | 2 |
| 14.40 | 6.15 | 71 |
| 15.33 | 5.78 | 19 |
| 16.09 | 5.50 | 5 |
| 18.07 | 4.90 | 41 |
| 18.64 | 4.76 | 21 |
| 19.62 | 4.52 | 41 |
| 19.92 | 4.45 | 46 |
| 20.65 | 4.30 | 4 |
| 21.10 | 4.21 | 46 |
| 21.44 | 4.14 | 36 |
| 21.66 | 4.10 | 32 |
| 22.13 | 4.01 | 21 |
| 22.35 | 3.97 | 20 |
| 22.99 | 3.86 | 10 |
| 23.86 | 3.73 | 15 |
| 24.36 | 3.65 | 50 |
| 24.75 | 3.59 | 17 |
| 25.02 | 3.56 | 3 |
| 25.66 | 3.47 | 10 |
| 26.06 | 3.42 | 4 |
| 26.35 | 3.38 | 10 |
| 27.66 | 3.22 | 13 |
| 28.01 | 3.18 | 1 |
| 28.44 | 3.14 | 8 |
| 29.20 | 3.06 | 1 |
| 30.16 | 2.96 | 4 |
| 30.43 | 2.94 | 2 |
| 30.96 | 2.89 | 20 |
| 31.44 | 2.84 | 8 |
| 32.48 | 2.75 | 7 |
| 33.21 | 2.69 | 2 |
| 33.74 | 2.65 | 2 |
| 34.15 | 2.62 | 2 |
| 34.81 | 2.58 | 5 |

Examples 4-7: General Procedure for the Synthesis of Various Acid Addition Salts of [2-(3-fluoro-5-methanesulfonylphenoxy)ethyl](propyl)amine The appropriate acid was added to an EtOH-solution of [2-(3-fluoro-5-methane-sulfonylphenoxy)ethyl](propyl)amine in ethanol and the mixture was heated to reflux until full dissolution, then cooled to room temperature. If precipitation occurred, the resultant solid was collected by filtration. The base/acid ratio of the obtained salts was determined by $^1$H NMR spectroscopy with a relaxation time of at least 10 seconds. Melting point was determined by DSC (Differential scanning calorimetry) and the solid-state characterization was determined by XRPD, which was used to determine if the precipitated salt was crystalline.

Example 4

Fumaric Acid Salt of [2-(3-fluoro-5-methanesulfonylphenoxy)ethyl](propyl)amine

The title salt was prepared according to the general procedure above. The salt was crystalline as determined by XRPD.

Yield: 78%.
Base/acid ratio: 2:1.
Melting point: 184.9° C.
Solubility in water: 92 mg/mL.

XRPD analysis provided the diffractogram in FIG. 2. The main characteristic peaks, with positions and relative intensities, have been extracted from the diffractogram in FIG. 2 and is given below in Table 2.

TABLE 2

Positions and intensities of the major peaks in the XRP-diffractogram of the salt of Formula Va which is a combination of the compound of Formula I and fumaric acid in a ratio of 1:0.5.

| Angle 2θ/° | d-value/Å | % Relative intensity |
|---|---|---|
| 7.62 | 11.6 | 42 |
| 11.17 | 7.92 | 1 |
| 12.66 | 6.98 | 4 |
| 12.98 | 6.82 | 12 |
| 13.79 | 6.42 | 1 |
| 15.27 | 5.80 | 100 |
| 15.54 | 5.70 | 6 |
| 16.23 | 5.46 | 1 |
| 16.64 | 5.32 | 1 |
| 18.55 | 4.78 | 11 |
| 18.88 | 4.70 | 2 |
| 19.15 | 4.63 | 2 |
| 19.51 | 4.55 | 2 |
| 19.92 | 4.45 | 4 |
| 21.10 | 4.21 | 2 |
| 21.47 | 4.14 | 2 |
| 21.84 | 4.07 | 12 |
| 22.60 | 3.93 | 5 |
| 22.65 | 3.92 | 8 |
| 22.98 | 3.87 | 22 |
| 23.47 | 3.79 | 1 |
| 24.08 | 3.69 | 9 |
| 24.89 | 3.57 | 1 |
| 25.34 | 3.51 | 2 |
| 25.78 | 3.45 | 3 |
| 26.01 | 3.42 | 3 |
| 27.47 | 3.24 | 1 |
| 28.62 | 3.12 | 1 |
| 29.33 | 3.04 | 1 |
| 29.52 | 3.02 | 1 |
| 30.79 | 2.90 | 7 |
| 31.40 | 2.85 | 3 |
| 32.83 | 2.73 | 1 |
| 33.11 | 2.70 | 1 |
| 34.00 | 2.64 | 1 |

Example 5

Maleic Acid Salt of [2-(3-fluoro-5-methanesulfonylphenoxy)ethyl](propyl)amine

The title salt was prepared according to the general procedure above. The salt was crystalline as determined by XRPD.
Yield: 88%.
Base/acid ratio: 1:1.
Melting point: 141.5° C.
Solubility in water: 35 mg/mL.

Example 6

Succinic Acid Salt of [2-(3-fluoro-5-methanesulfonylphenoxy)ethyl](propyl)amine

The title salt was prepared according to the general procedure above with the exception that the solution was cooled to −18° C. until precipitation occurred. The salt was crystalline as determined by XRPD.
Yield: 75%.
Base/acid ratio: 1:1.
Melting point: 109.2° C.
Solubility in water: 285 mg/mL.

Example 7

L-Tartaric Acid Salt of [2-(3-fluoro-5-methanesulfonylphenoxy)ethyl](propyl)amine The title salt was prepared according to the general procedure above. The salt was crystalline as determined by XRPD.
Yield: 73%.
Base/acid ratio: 2:1.
Melting point: 187.6° C.
Solubility in water (regular water solubility test): 185 mg/mL.
Solubility in water (flask method water solubility test): 252.6 mg/mL.

Comparative Example (Water Solubility)

In comparative tests for the determination of the water solubility for the hydrochloric acid salt of [2-(3-fluoro-5-methanesulfonylphenoxy)-ethyl](propyl)amine it was concluded that said hydrochloric acid salt (i.e. Example 1 of WO 2012/143337) had a water solubility of 197 mg/mL (regular water solubility test) and 270 mg/mL (flask method water solubility test), respectively.

Hygroscopicity Determination of the L-Tartaric Acid Salt of [2-(3-fluoro-5-methanesulfonylphenoxy)ethyl](propyl)amine According to Example 7

TABLE 3

| Relative Humidity (%) | Weight difference (%) Example 7 |
|---|---|
| 0 | −0.26 |
| 6 | 0.00 |
| 11 | −0.06 |
| 22 | 0.12 |
| 33 | −0.18 |
| 45 | −0.13 |
| 56 | −0.15 |
| 73 | −0.24 |
| 75 | −0.07 |
| 83 | 0.06 |
| 97 | −0.08 |

As shown in Table 3, the L-tartaric acid salt of [2-(3-fluoro-5-methanesulfonylphenoxy)ethyl](propyl)amine according to Example 7 does not adsorb or desorb any significant amount of water at any humidity. Thus, the salt has a very low hygroscopicity, i.e. a weight change of 0.3% or less, even when it is exposed to a very high relative humidity such as 73%, 75%, 83% or 97% for 7 days at 30° C.

Comparative Example (Hygroscopicity)

In another test utilizing the DVS technique for the determination of the hygroscopicity for the hydrochloric acid salt of [2-(3-fluoro-5-methanesulfonylphenoxy)-ethyl](propyl)

amine it was concluded that said hydrochloric acid salt (i.e. Example 1 of WO 2012/143337) gained approximately 3% of weight at 95% relative humidity and 25° C. The cycles were repeatable.

Remarks

As can be seen in the Examples above, the maleic acid salt has a low solubility and a relatively low melting point whereas the succinic acid salt has a very good solubility but a low melting point. On the other hand, the fumaric acid salt, and in particular, the L-tartaric acid salt have high melting points as well as high solubilities in water. Also, even though the hydrochloric acid salt according to Example 1 of WO 2012/143337 has a high melting point and high water solubility, it is hygroscopic at high relative humidities. The L-tartaric acid salt according to the present disclosure is not hygroscopic at any relative humidities. These beneficial physical properties taken together make the fumaric acid salt and in particular the L-tartaric acid salt of [2-(3-fluoro-5-methanesulfonyl-phenoxy)ethyl](propyl)amine very good drug candidates when it comes to possessing pharmaceutical properties, i.e. properties making it suitable for use as a pharmaceutical, such as handling and/or storage properties.

Human Clinical Study in Parkinson's Patients with L-Dopa Induced Dyskinesia (LIDs) Using the L-Tartaric Acid Salt of [2-(3-fluoro-5-methanesulfonyl-phenoxy)ethyl](propyl)amine of Example 7

Home diaries have gained wide acceptance as endpoints for clinical development of therapeutics aiming to reduce treatment-related motor complications [2]. Motor fluctuations are associated with compromise in activities of daily living and health-related quality of life. In clinical trials performed by Integrative Research Laboratories Sweden AB patients record their 24-hours motor function in 30-minute intervals, beginning at midnight. For each 30-minute interval the patient rates the state he or she has been in for the past 30 minutes; OFF, ON without troublesome dyskinesia or ON with troublesome dyskinesia. The patient also denoted the time when he or she has been asleep. It has been demonstrated that OFF-time and ON-time with troublesome dyskinesia are generally considered by patients to be "bad time" with regard to motor function, whereas ON-time without dyskinesia and ON-time without troublesome dyskinesia are generally considered to be "good ON-time" [3, 4].

In general, an "OFF" time reduction or "good ON-time" increase of 1 hour may be considered clinically significant and has been used as an assumption in power calculations in clinical trials [2]. Therefore, it can be assumed that shift towards more "good ON-time" of a minimum of 1-hour daily represents a clinically meaningful effect, considering the total time spent in the daily ON state (ON with and without troublesome dyskinesia) is not negatively affected by the treatment.

For inclusion in the clinical trial, patients must demonstrate ability to complete the 24-hour patient home diaries. A valid diary is defined as not having more than 2 hours of invalid data entries (4 invalid entries) over a given 24-hour period. An invalid diary entry is defined as more than one entry recorded in each half-hour interval, an unreadable entry, or the absence of an entry in each half-hour interval. The average diary information from 3 valid diaries (if available) for each visit will be used to calculate diary-based efficacy endpoints. If there are only 2 valid diaries for a visit, then the average information from the 2 valid diaries will be used. If only one diary is valid, information from the single valid diary will be used. If no valid diaries were available for a patient visit, then the diary information was considered missing.

Method

At run-in and following treatment patients were asked to complete home diaries describing their motor status in 30-minute intervals for 24 hours. Patients were asked to describe their past 30-minute motor status in one of four categories: Asleep, OFF, ON, or ON with troubling dyskinesia. Descriptions of each category were included in the diary as follows:

ON: Good or practically normal mobility.

ON with troubling dyskinesia: Troubled by involuntary twisting, turning movements. These movements are different from the rhythmic "tremor" which is a symptom of Parkinson's Disease itself.

OFF: Stiffness, marked decrease in mobility, or immobility.

Asleep: Time spent asleep.

Results and Conclusion

It has been found in human studies that through reduction in troublesome dyskinesias (LIDs) in patients suffering from Parkinson's Disease treated with L-DOPA (levodopa) resulted in more daily hours of good mobility (good ON time) at plasma concentrations of 50-200 nM of the drug measured 2 hours after administration of drug in the morning. This plasma concentration range was obtained by administering to patients 2.5 mg b.i.d.-10 mg b.i.d. of the L-tartaric acid salt of [2-(3-fluoro-5-methanesulfonyl-phenoxy)ethyl](propyl)amine. The doses (2.5 mg-10 mg) are calculated on the non-salt form of [2-(3-fluoro-5-methanesulfonyl-phenoxy)ethyl](propyl)amine.

Table 4. Improvement in Good ON time (i.e. the time the patient indicated as "ON" meaning good or practically normal mobility) in Parkinson's patients with L-dopa induced dyskinesia (LIDs) using the L-tartaric acid salt of [2-(3-fluoro-5-methanesulfonyl-phenoxy)ethyl](propyl) amine according to Example 7 or placebo.

TABLE 4

| Dose treatment twice-daily (b.i.d.) | Improvement in good ON time (mean values) | Number of patients |
|---|---|---|
| 5 mg or less (2.5 mg in some patients) | 2.1 h | 9 |
| 7.5 mg | 5.6 h | 8 |
| 10 mg or more (12.5 mg in some patients) | 1.4 h | 20 |
| Placebo | 1.0 | 34 |

It was concluded that administration of [2-(3-fluoro-5-methanesulfonyl-phenoxy)ethyl](propyl)amine in an amount from 2.0 mg up to 10 mg such as 2.5 mg, 5.0 mg or 7.5 mg to a patient suffering from Parkinson's disease resulted through reduction in troublesome dyskinesia (LIDs) in more daily hours of good mobility (good ON time). Further, it was concluded that administration of [2-(3-fluoro-5-methanesulfonyl-phenoxy)ethyl](propyl)amine in an amount from 2.0 mg up to 10 mg such as 2.5 mg, 5.0 mg or 7.5 mg increased the good ON time to a larger extent than administration of [2-(3-fluoro-5-methanesulfonyl-phenoxy) ethyl](propyl)amine in an amount equal to or above 10 mg.

REFERENCES

1. WO 2012/143337
2. Papapetropoulos S S. Patient diaries as a clinical endpoint in Parkinson's disease clinical trials. *CNS Neurosci Ther.* 2012; 18:380-7
3. Hauser R A, Friedlander J, Zesiewicz T A, et al. A home diary to assess functional status in patients with Parkinson's disease with motor fluctuations and dyskinesia. Clin Neuropharmacol 2000; 23:75-81
4. Hauser R A, Deckers F, Lehert P. Parkinson's disease home diary: Further validation and implications for clinical trials. Movement Disorders 2004, 19 (12), 1409-1413.

The invention claimed is:

1. A salt of Formula IVa being a combination of a compound of Formula I and tartaric acid:

wherein said salt is crystalline.

2. The salt of Formula IVa according to claim 1, wherein the tartaric acid is L-(+)-tartaric acid and/or D-(−)-tartaric acid.

3. The salt of Formula IVa according to claim 1, characterized by an XRP diffractogram comprising a peak at 13.0 2θ and one or more peaks selected from the following: 12.4, 14.4, 21.1, 24.4 2θ.

4. The salt of Formula IVa according to claim 1, characterized by an XRP diffractogram comprising peaks at 13.0, 12.4, 14.4, 21.1 and 24.4 2θ.

5. The salt of Formula IVa according to claim 1, characterized by an XRP diffractogram as shown in FIG. 1.

6. A pharmaceutical composition comprising the salt of Formula IVa according to claim 1 in admixture with a pharmaceutically acceptable excipient, carrier and/or diluent.

7. The pharmaceutical composition according to claim 6 comprising the compound of Formula IVa in an amount from 2.0 mg up to 10.0 mg.

8. The pharmaceutical composition according to claim 7, wherein the amount of the compound of Formula IVa is 2.5 mg, 5.0 mg or 7.5 mg.

9. The pharmaceutical composition according to claim 6, wherein the pharmaceutical composition is provided in a single dosage form.

10. The pharmaceutical composition according to claim 6, wherein the salt of Formula IVa has a degree of crystallinity of 80% or more.

11. A method for preparing the salt of Formula IVa according to claim 1, said method comprising the steps of:
   providing the compound of Formula I and tartaric acid in a ratio of 1:0.5,
   combining said compound of Formula I with said tartaric acid in a solvent to form a solution, and
   allowing said solution to stand until a precipitate forms, and
   isolating said precipitate by filtration thereby providing the salt of Formula IVa.

12. The method according to claim 11, wherein said solvent is a mixture of solvents.

13. The method according to claim 11, wherein said solvent comprises ethanol.

14. The method according to claim 11, wherein the step of forming a precipitate is performed at a temperature of 20° C. to 25° C.

15. The salt of Formula IVa according to claim 1, wherein the tartaric acid is L-(+)-tartaric acid.

16. The salt of Formula IVa according to claim 1, wherein the tartaric acid is D-(−)-tartaric acid.

17. The salt of Formula IVa according to claim 1, wherein the tartaric acid is L-(+)-tartaric acid and D-(−)-tartaric acid.

* * * * *

UNITED STATES PATENT AND TRADEMARK OFFICE
CERTIFICATE OF CORRECTION

| | | |
|---|---|---|
| PATENT NO. | : 12,275,694 B2 | Page 1 of 1 |
| APPLICATION NO. | : 17/612902 | |
| DATED | : April 15, 2025 | |
| INVENTOR(S) | : Reine et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 659 days.

Signed and Sealed this
Sixteenth Day of December, 2025

John A. Squires
*Director of the United States Patent and Trademark Office*